(12) United States Patent
Kilmer et al.

(10) Patent No.: US 9,989,493 B2
(45) Date of Patent: *Jun. 5, 2018

(54) ELECTROBLOT TRANSFER BUFFER

(71) Applicant: Pierce Biotechnology, Inc., Rockford, IL (US)

(72) Inventors: Gregory John Kilmer, Winnebago, IL (US); Brian David Wolf, Manchesney Park, IL (US); Scott Eugene Starwalt, Byron, IL (US); Gary G Judd, DeKalb, IL (US); Brian Lynn Webb, Roscoe, IL (US)

(73) Assignee: PIERCE BIOTECHNOLOGY, INC., Rockford, IL (US)

( * ) Notice: Subject to any disclaimer, the term of this patent is extended or adjusted under 35 U.S.C. 154(b) by 44 days.

This patent is subject to a terminal disclaimer.

(21) Appl. No.: 15/043,816

(22) Filed: Feb. 15, 2016

(65) Prior Publication Data
US 2016/0266065 A1   Sep. 15, 2016

Related U.S. Application Data

(63) Continuation of application No. 13/764,934, filed on Feb. 12, 2013, now Pat. No. 9,291,596.

(51) Int. Cl.
*G01N 27/447* (2006.01)

(52) U.S. Cl.
CPC . *G01N 27/44747* (2013.01); *G01N 27/44739* (2013.01)

(58) Field of Classification Search
CPC ......... G01N 27/4472; G01N 27/44739; G01N 33/5308; G01N 33/558; G01N 33/559; G01N 33/552; G01N 2440/00–2440/40; G01N 2458/00–2458/40; B01D 57/02; G10N 2410/00–2410/10; C07K 1/24–1/285

See application file for complete search history.

(56) References Cited

U.S. PATENT DOCUMENTS 4,139,440 A   2/1979   Chrambach et al.
4,452,901 A   6/1984   Gordon et al.
(Continued)

FOREIGN PATENT DOCUMENTS

| | | |
|---|---|---|
| JP | 2002-257721 | 9/2002 |
| WO | 2005/094539 | 10/2005 |
| WO | 2007/126506 | 11/2007 |

OTHER PUBLICATIONS

Towbin et al. Electrophoretic transfer of proteins from polyacrylamide gels to nitrocellulose sheets: Procedure and some applications, Proc. Nat. Acad. Sci. vol. 76, No. 9, (1979), pp. 4350-4354.
(Continued)

*Primary Examiner* — J. Christopher Ball
(74) *Attorney, Agent, or Firm* — Baker & Hostetler LLP

(57) ABSTRACT

A semi-dry, one step electroblot transfer buffer composition for rapid transfer of proteins or polypeptides from polyacrylamide gel to a suitable membrane such as nitrocellulose or polyvinylidene difluoride (PVDF). The composition contains components that minimized electrical resistance and enabled high efficiency rapid semi-dry transfer using conventional readily available filter paper, i.e., cotton cellulose fiber.

21 Claims, 5 Drawing Sheets

(56) References Cited

U.S. PATENT DOCUMENTS

| | | | |
|---|---|---|---|
| 4,589,965 | A | 5/1986 | Kreisher |
| 4,840,714 | A | 6/1989 | Littlehales |
| 4,870,714 | A | 6/1989 | Littlehales |
| 4,889,606 | A | 12/1989 | Dyson et al. |
| 5,013,420 | A | 5/1991 | Schuette |
| 5,173,159 | A | 12/1992 | Dutertre |
| 5,256,772 | A | 10/1993 | Ohtomo |
| 5,356,772 | A | 10/1994 | Chan |
| 5,445,723 | A | 8/1995 | Camacho |
| 5,482,613 | A | 1/1996 | Boquet |
| 6,162,338 | A | 12/2000 | Updyke et al. |
| 6,379,516 | B1 | 4/2002 | Cabilly et al. |
| 6,592,734 | B2 | 7/2003 | Chen |
| 6,602,661 | B1 | 8/2003 | Knezevic et al. |
| 8,075,755 | B2 | 12/2011 | Yang |
| 8,173,002 | B2 | 5/2012 | Margalit et al. |
| 9,291,596 | B2 * | 3/2016 | Kilmer ............ G01N 27/44747 |
| 2002/0012920 | A1 | 1/2002 | Gardner et al. |
| 2002/0157953 | A1 | 10/2002 | Chen |
| 2005/0000811 | A1 | 1/2005 | Luka |
| 2005/0009036 | A1 | 1/2005 | Montesclaros et al. |
| 2005/0121325 | A1 | 6/2005 | Updyke et al. |
| 2006/0272946 | A1 | 12/2006 | Margalit et al. |
| 2006/0278531 | A1 | 12/2006 | Margalit et al. |
| 2009/0026079 | A1 | 1/2009 | Margalit et al. |
| 2009/0183989 | A1 | 7/2009 | Yang |
| 2010/0213060 | A1 | 8/2010 | Chmiel |

OTHER PUBLICATIONS

Timmons and Dunbar, Protein Blotting and Immunodetection, Methods in Enzymology, vol. 182 (1990), pp. 679-688.

Daban, Joan-Ramon; "Fluorescent labeling of proteins with Nile red and 2-methoxy-2,4-diphenyl-3(2H)-furanone: Physicochemical basis and application to the rapid staining of sodium dodecyl sulfate polyacrylamide gels and Western Blots"; Electrophoresis, vol. 22; pp. 874-880 (2001).

Zeng, C. et al.; "Polyethylene Glycol Significantly Enhances the Transfer of Membrane Immunoblotting"; Analytical Biochemistry; Vo. 189; pp. 197-201 (1990).

Kurien, Biji T. et al.; "Protein Blotting: a review"; Journal of Immunological Methods; vol. 274, No. 1-2; pp. 1-15 (Mar. 1, 2003).

Pachulski, Nadine, et al.; "Production of Tablet-Like Solid Bodies Without Pressure by Sol-Gel Processes"; Letters in Drug Design & Discovery; vol. 4; pp. 78-81 (2007).

Genscript Corporation; "One-Step Western Blot Kit, Technical Manual No. 0184"; pp. 1-5 (Mar. 25, 2008)).

Genscript Corporation; "One-Step Western Kit, Technical Manual No. 0184"; pp. 1-5 (Apr. 3, 2007).

PCT, International Search Report and Written Opinion; Application No. PCT/US2006/005933 dated (Sep. 12, 2007).

PCT, International Preliminary Report on Patentability; Application No. PCT/US2009/050333 dated (Jan. 20, 2011).

* cited by examiner

ELECTROBLOT TRANSFER BUFFER

This application is a continuation of U.S. application Ser. No. 13/764,934 filed Feb. 12, 2013, now U.S. Pat. No. 9,291,598, which is expressly incorporated by reference herein in its entirety.

Electroblotting is a method to transfer proteins and/or nucleic acids that have been separated by gel electrophoresis onto a membrane, such as polyvinylidene difluoride (PVDF) or nitrocellulose. The gel containing proteins and/or nucleic acids is placed next to a membrane and then sandwiched between filter paper, i.e., cotton cellulose fiber, either immersed or saturated in suitable transfer buffer. The resulting sandwich or transfer stack is composed of the gel and membrane positioned in between two sheets of filter paper in a specific orientation, i.e., membrane between gel and anode.

Figure 1:
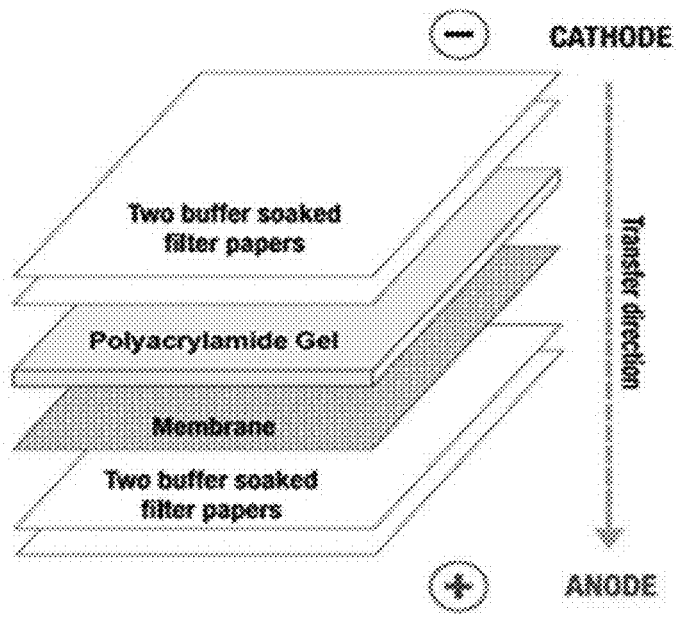
FIG. 1 schematically shows "sandwich" components and methods for electroblot transfer.

Electroblotting can be performed with the transfer stack either completely immersed in transfer buffer, i.e., a "wet" transfer, or with the filter paper saturated with transfer buffer, i.e., "semi-dry transfer". In either type of transfer, current is directed through the transfer stack to drive the negatively charged molecules towards the anode and onto the membrane (FIG. 1). The proteins or nucleic acids are then analyzed on the membrane using probes, such as specific antibodies, using a western blotting protocol.

For semi-dry transfers, the transfer buffer contained in the filter paper provides the necessary ions, i.e., ion reservoir, for electroblotting transfer. Conventional semi-dry transfer buffers, e.g. 25 mM tris, 192 mM glycine, 20% ethanol, have relatively low ionic strength resulting in low current (2 $mA/cm^2$ to 3 $mA/cm^2$) and high resistance (>10 $\Omega/cm^2$) during electroblotting. These conditions typically require transfer times of greater than 60 minutes for optimal transfer of proteins to the membrane. Transfer buffers have been disclosed, e.g., Towbin, Proc. Natl. Acad. Sci. USA 76 (1979) 4350-4354 and Timmins, Methods in Enzymology 182 (1990) 679-688.

More rapid semi-dry electroblot transfers can be achieved by increasing the ionic strength of the transfer buffer, e.g. 300 mM tris, 300 mM glycine, 0.1% SDS, and 20% ethanol, as disclosed in U.S. Patent Application Publication No. 2010/0212060. Such high ionic strength transfer buffers result in higher current flow during the transfer, allowing efficient transfers in ten minutes or less. U.S. Pat. No. 8,075,755 discloses that, in order to avoid excess heat generated during high current semi-dry electroblotting, absorbent materials other than conventional filter paper must be used in the transfer stack, such as multilayered sheets of polyester or polyester/cellulose blends. The use of these alternative polyester materials in semi-dry blotting transfer stacks enables higher current and lower resistance and thus lower heat generation during rapid electroblotting. The combination of high ionic strength transfer buffer with polyester/cellulose filter material allows for dramatically reduced transfer time.

The inventive method optimized a semi-dry electroblotting transfer buffer composition that resulted in rapid electroblotting without excessive heat generation due to high resistance during high current electroblot transfers using conventional filter paper, i.e., cotton cellulose fiber as the absorbent material, in the transfer stack. The inventive transfer buffer composition enabled efficient and rapid electrotransfer of protein and/or polypeptides from gels to either nitrocellulose or PVDF membrane using conventional cotton cellulose fiber filter paper without excessive heat generation. Such transfers can be used for western blotting and other procedures.

Conventional transfer buffers typically contain tris(hydroxymethyl)aminomethane (tris) and glycine. The inventive electroblotting transfer buffer composition contains tris, glycine, N-(2-hydroxy-1,1-bis(hydroxymethyl)ethyl)glycine (tricine), and optionally ethylenediaminetetraacetic acid (EDTA). Tricine has not been used as a component in electroblotting transfer buffers, although it has been used in gel electrophoresis buffer. The addition of tricine and optionally EDTA to the transfer buffer eliminated the need to use less conventional and more expensive polyester or polyester/cellulose blend materials in the electroblot transfer stack and resulted in efficient transfer.

In one embodiment, the inventive electroblot transfer buffer composition contained tris in the range of 250 mM to 1,000 mM inclusive, glycine in the range of 250 mM to 1,000 mM inclusive, N-(2-hydroxy-1,1-bis(hydroxymethyl) ethyl)glycine (tricine) in the range of 100 mM to 1,000 mM inclusive, and in embodiments using EDTA, EDTA in the range of 1 mM to 100 mM inclusive. In one embodiment, the inventive electroblot transfer buffer composition contained tris in the range of 250 mM to 350 mM inclusive, glycine in the range of 250 mM to 350 mM inclusive, tricine in the range of 100 mM to 200 mM inclusive, and in embodiments using EDTA, EDTA in the range of 1 mM to 5 mM inclusive. In one embodiment, the inventive electroblot transfer buffer composition contained about 336 mM tris, about 260 mM glycine, about 140 mM tricine, and in embodiments using EDTA, about 2.4 mM EDTA.

The addition of tricine and optionally EDTA to concentrated tris/glycine transfer buffer resulted in a one-step transfer buffer that eliminated the need for specialized multilayered polyester cellulose material to reduce resistance during rapid, high current electroblotting. Using concentrated tris/glycine transfer buffer without tricine and optionally EDTA with conventional filter paper as the absorbent material resulted in high electrical resistance during electroblotting.

Figure 2:
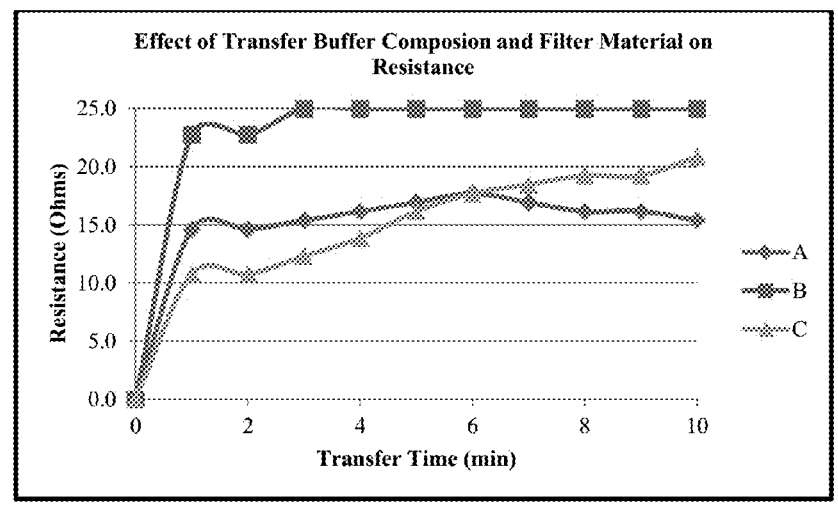
FIG. 2 shows electrical resistance versus time during electroblotting using different buffer compositions.

FIG. 2 shows electrical resistance versus time during electroblotting using the following buffer compositions: (A) 300 mM tris, 300 mM glycine, 0.1% sodium dodecyl sulfate (SDS), 20% EtOH using polyester/cellulose filter paper; (B) 300 mM tris, 300 mM glycine, 0.1% SDS, 20% EtOH using cotton cellulose fiber filter paper; and (C) 336 mM tris, 260 mM glycine, 140 mM tricine, 2.5 mM EDTA using cotton cellulose fiber filter paper.

It was previously demonstrated that polyester/cellulose filter as the absorbent material in the transfer stack can reduce the electrical resistance, leading to less heat generation during the electroblotting transfer. However, polyester/cellulose materials are expensive. The inventive tris/glycine buffer containing tricine and optionally EDTA, allowed the use of traditional cotton cellulose fiber filter paper to efficiently transfer polypeptides from gel to membrane during the course of high current electroblotting. As shown in FIG. 2, the addition of tricine and EDTA to concentrated tris/glycine transfer buffers (A and C) resulted in reduced electrical resistance, from 7.0 to 4.1 $m\Omega/cm^2$, during electroblotting.

In one embodiment, conventional cotton cellulose fiber filter paper was equilibrated in the disclosed electroblot transfer buffer composition. It was then used in assembly of the electroblotting "sandwich" components of the polyacrylamide gel, and either nitrocellulose or PVDF membrane, as shown in FIG. 1. A high current power supply was used to pass current through the "sandwich", with the buffer components acting as an ion reservoir to move ions from the cathode to the anode, with the separated proteins and/or polypeptides of interest contained in the polyacrylamide gel matrix moving from the gel onto the membrane, i.e., electroblotting.

The inventive electroblot transfer buffer composition efficiently effected such transfer using conventional cotton cellulose fiber filter paper. The effect of different transfer buffer compositions and transfer stack materials, e.g., conventional filter paper and polyester/cellulose material, on electrical resistance during electroblotting was demonstrated using either traditional cotton cellulose fiber filter paper or multilayered polyester/cellulose sheets, as shown in FIG. 2. For each buffer and filter paper composition, electroblotting was performed using the following method: protein was transferred from a mini-polyacrylamide gel to a nitrocellulose membrane using 1.3 Amps (constant), 25 volts (limit), for ten minutes. High concentration tris/glycine buffer was tested with polyester/cellulose material (A) or conventional filter paper (B and C) in the transfer stack. The electrical resistance was significantly lower using the polyester/cellulose material, as disclosed in U.S. Pat. No. 8,075,755. This lower resistance resulted in higher current and less heat generation. However, polyester/cellulose materials are more expensive than conventional cotton fiber filter paper.

In embodiments, the inventive electroblot transfer buffer composition may contain components that, in some embodiments, may enhance ease of use and/or provide a specific user with a desired benefit but that do not affect the basic characteristics of the transfer buffer. Examples of such components include an ionic detergent such as sodium dodecyl sulfate (SDS), and/or an alcohol such as ethanol.

Low electrical resistance during electroblotting transfer was achieved with conventional filter paper when tricine and EDTA were included in the transfer buffer (C). The inclusion of tricine and optionally EDTA with tris and glycine in the transfer buffer resulted in relatively lower resistance. The average resistance during the ten minute electroblotting was reduced from 7.0 $m\Omega/cm^2$ to 4.1 $m\Omega/cm^2$ and current flow was increased from 1.0 Amps to 1.3 Amps. Thus, the addition of tricine and optionally EDTA enabled the use of inexpensive conventional filter paper for rapid, efficient electroblot transfer.

In one embodiment, the concentration effects of an electroblot transfer buffer composition containing tris, glycine, tricine, ethanol, and cyclodextrin on protein transfer efficiency were evaluated using a two level five factor central composite factorial design. Factorial experimental designs allow for the investigation of multiple factors at once to identify interactions between the factors tested. Tricine, tris, and glycine concentrations were identified as significant factors that improved rapid electroblotting of proteins, including larger proteins (100 kDa-250 kDa). The addition of tricine as an electroblot transfer buffer component reduced the concentrations of tris and glycine that were required. This provided a more robust transfer buffer that was resilient to changes in tris and glycine concentrations and reduced resistance during electroblotting with conventional filter paper. Increasing the tricine concentration from 50 mM to 200 mM, decreased the current change during protein transfer, and allowed for rapid electroblotting without excessive heat generation.

Figure 3:
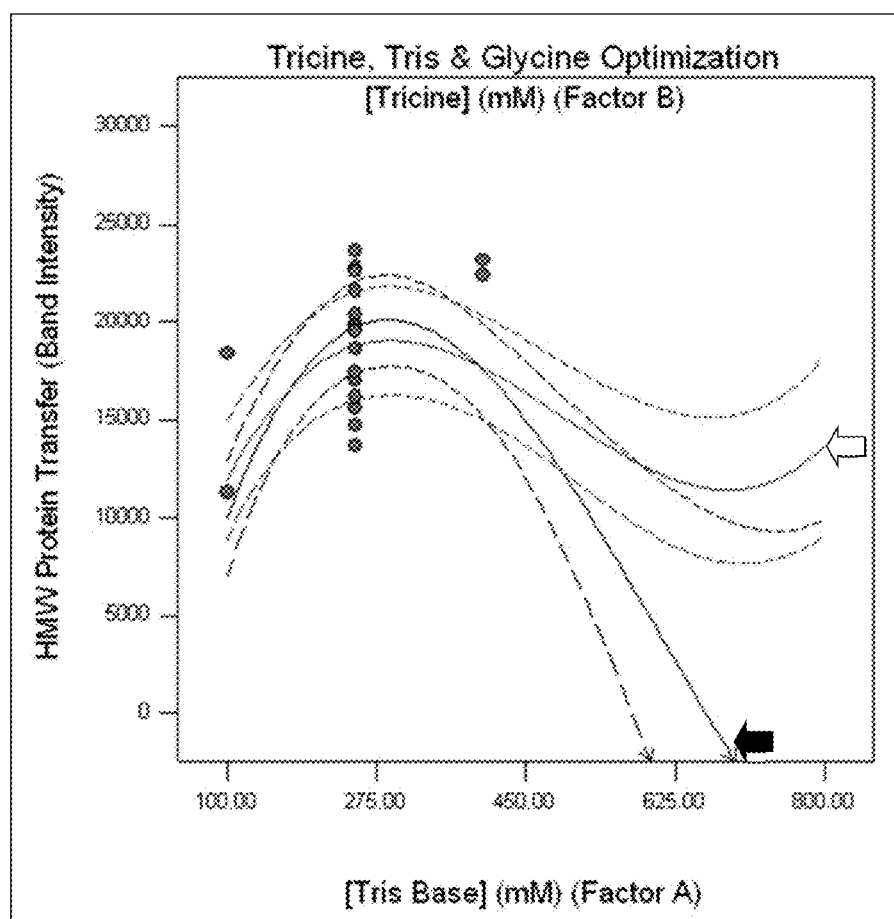
FIG. 3 shows tris(hydroxymethyl)aminomethane (tris), glycine, and N-(2-hydroxy-1,1-bis(hydroxymethyl)ethyl) glycine (tricine) optimization.

FIG. 3 shows the effect of the electroblot transfer buffer tris concentration (x-axis, Factor A) with high (200 mM, open white arrow) and low (50 mM, filled black arrow) tricine concentrations, with 325 mM glycine on protein transfer as measured by densitometry. The graph shows the tris concentration versus band intensity for 200 mM (solid line highlighted by white arrow) and 50 mM (solid line highlighted by black arrow) tricine concentrations. Solid lines show the mathematical response model for high molecular weight (HMW) protein and the dotted lines represented the confidence interval of the mathematical model. Dots represent the experimental data points.

These data resulted from varying the concentration of each factor in a designed experiment where predictive output responses were collected for each model generated testing point. The factors tested were tris concentration (100 mM-800 mM), tricine concentration (50 mM-200 mM), and glycine concentration (50 mM-1,000 mM). Three outputs were measured to determine the optimal transfer buffer composition: (1) densitometry of pre-stained broad range molecular weight (10 kDa to 250 kDa) protein standards that transferred to nitrocellulose membrane; (2) densitometry of pre-stained high molecular weight (100 kDa to 250 kDa) protein standards that transferred to nitrocellulose membrane, and (3) densitometry of pre-stained broad range molecular weight (10 kDa to 250 kDa) protein standards that remained in the polyacrylamide gel after transfer. The densitometry of the bands was performed using a myECL™ Imager (Thermo Scientific) and analyzed using myImageAnalysis™ software (Thermo Scientific). Solid lines showed the mathematical response model for high molecular weight (HMW) protein transfer that was used to predict optimum tricine, tris, and glycine concentrations. Dotted lines represented the confidence interval of the mathematical model. Circles were the experimental data points. As shown in FIG. 3, with only 50 mM tricine in the formulation, there was a significant decrease in high molecular weight protein transfer as the tris concentration deviated from 300 mM; however, with a higher concentration of tricine, 200 mM, the tris concentration had less effect on protein transfer efficiency using conventional cotton cellulose fiber filter paper.

Figure 4:
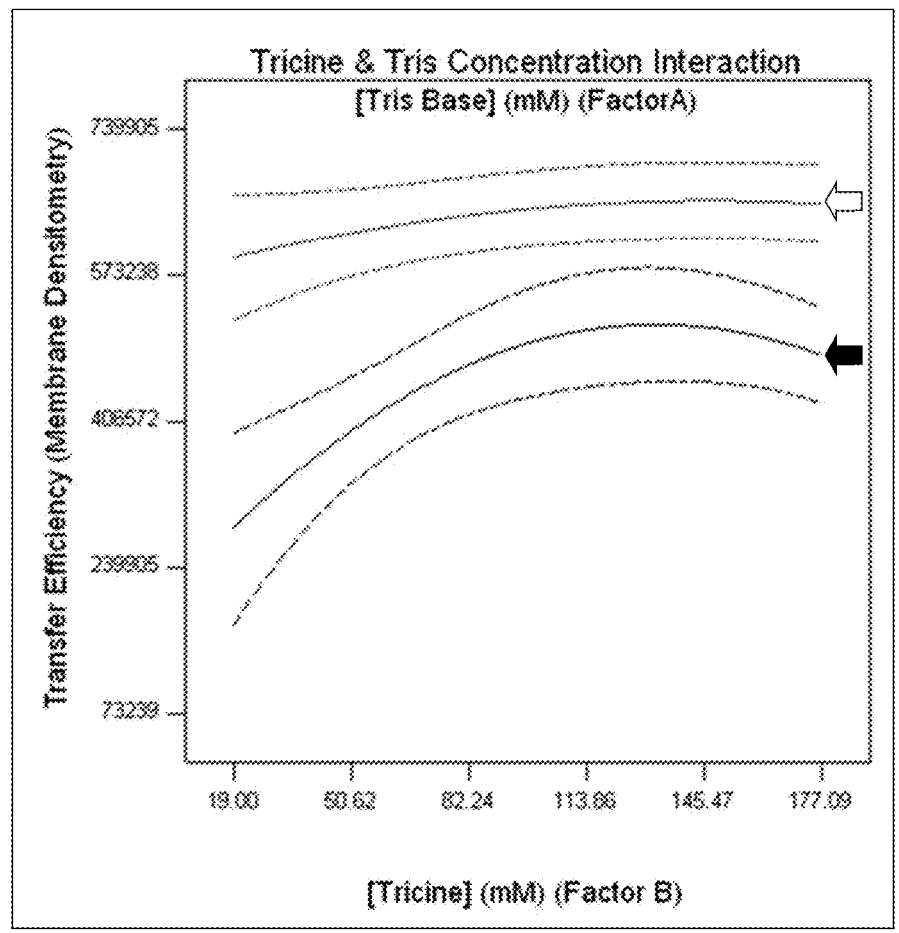
FIG. 4 shows tricine and tris concentration interaction.

FIG. 4 shows the effect of electroblot transfer buffer tricine concentration (x-axis, Factor B) with high (400 mM, open white arrow) and low (100 mM, solid black arrow) tris, with 95 mM glycine concentrations on protein transfer as measured by densitometry. The graph shows the tricine concentration versus transfer efficiency in terms membrane densitometry for 400 mM (solid line highlighted by white arrow) and 100 mM (solid line highlighted by black arrow) tris concentrations at 95 mM glycine. Solid lines show the mathematical response model for transfer efficiency, measured by membrane band intensity, used to predict optimum tricine, tris, and glycine concentrations. Dotted lines represented the confidence interval of the mathematical model.

The data demonstrated that achieving the desired protein transfer efficiency using conventional cotton cellulose fiber filter paper required the use of lower tris and glycine concentrations. Lower concentrations of tris were feasible by increasing the tricine concentration in the electroblot transfer buffer composition. The addition of tricine also reduced the concentration of glycine required.

Figure 5A:
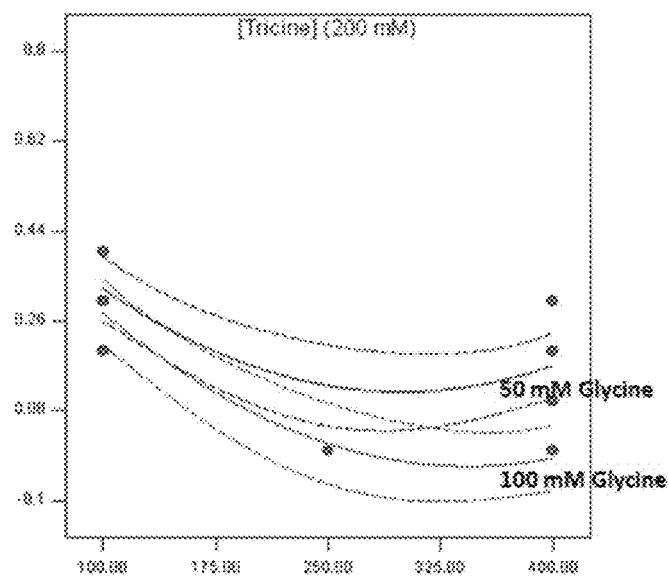
FIGS. 5A, 5B show the effect of tricine at each of 50 mM (FIG. 5A) and 200 mM (FIG. 5B) with varying concentrations of tris and glycine on change in current during electroblot transfer.
Figure 5B:
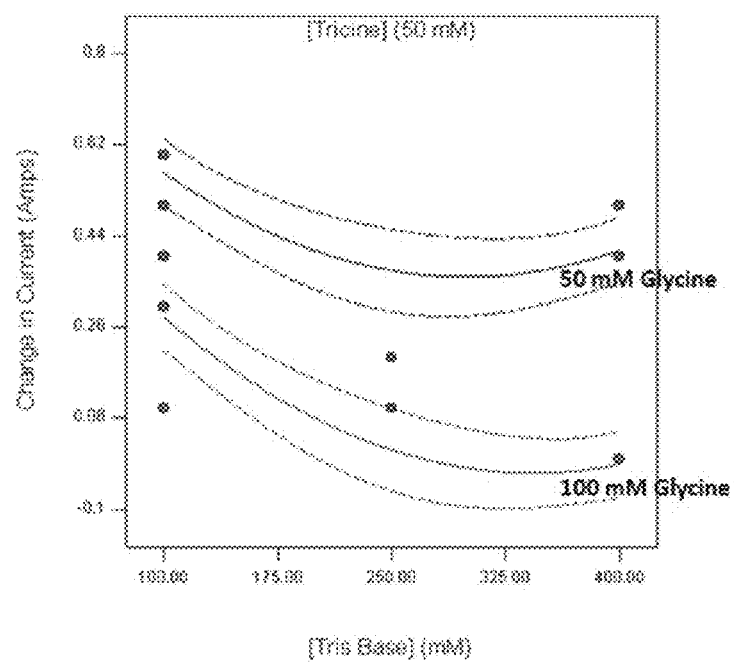

FIGS. 5A, 5B show the effect of 50 mM (FIG. 5A) and 200 mM (FIG. 5B) with varying concentrations of tris and glycine on change in current during electroblot transfer. Solid lines show the mathematical response model for change in current and the dotted lines represented the confidence interval of the mathematical model. Dots represent the experimental data points. As shown in FIG. 5, the effect of tricine at 50 mM (A) and 200 mM (B), tris, and glycine concentrations on the current change during electroblot transfers with conventional cotton cellulose fiber filter paper was determined. Increasing the tricine concentration from 50 mM to 200 mM reduced the current change when using lower concentrations, 50 mM, of glycine in the electroblot transfer buffer. The lower current change indicated a lower resistance during electroblot transfer.

Figure 6:
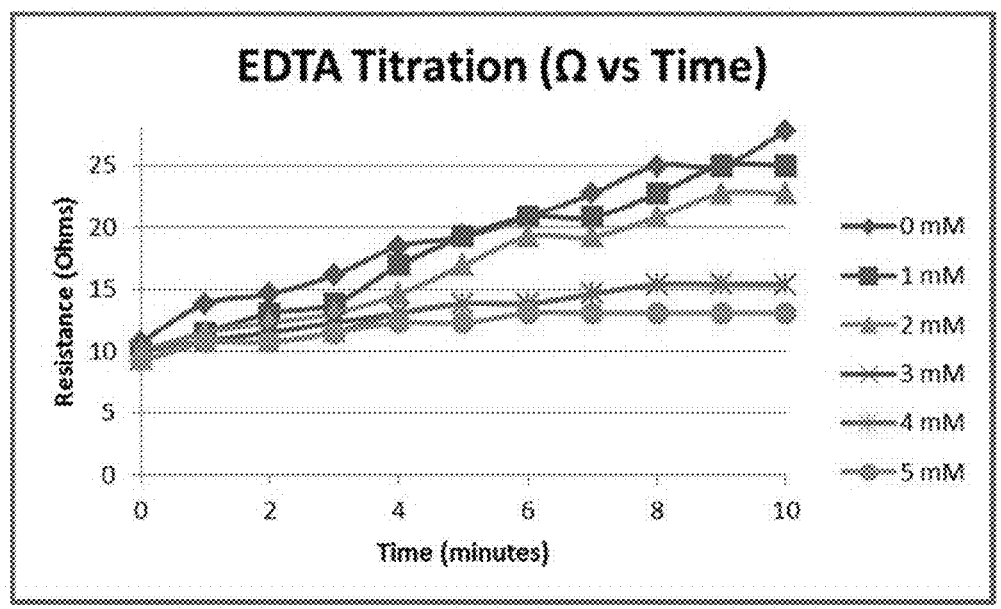
FIG. 6 shows the effect of ethylenediaminetetraacetic acid (EDTA) titration in resistance versus time during electroblot transfer.

FIG. 6 shows the effect of titrating ethylenediaminetetraacetic acid (EDTA) in 336 mM tris, 260 mM glycine, and 140 mM tricine, from 1 to 5 mM using traditional cotton cellulose fiber filter paper. An EDTA concentration greater than 2 mM showed the lowest resistance during electroblot transfer.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. An electroblot transfer method comprising:
    assembling a membrane and a gel, the gel containing at least one of separated proteins, peptides, or nucleic acids, the membrane and the gel sandwiched between at least two pieces of absorbent material, the absorbent material saturated with a transfer buffer comprising N-(2-hydroxy-1,1-bis(hydroxymethyl)ethyl)glycine (tricine), and glycine, to form a semi-dry stack; and
    applying a current to effect reduced resistance in transfer of at least one of the separated proteins, polypeptides, or nucleic acids from the gel to the membrane in a semi-dry blotting procedure.

2. The method of claim 1 wherein the absorbent material is a cotton cellulose paper.

3. The method of claim 1 wherein the absorbent material is polyester cellulose.

4. The method of claim 1 wherein the transfer buffer comprises tris(hydroxymethyl)aminomethane (tris) in the range of 250 mM to 1,000 mM inclusive, glycine in the range of 250 mM to 1,000 mM inclusive, and N-(2-hydroxy-1,1-bis(hydroxymethyl)ethyl)glycine (tricine) in the range of 100 mM to 1,000 mM inclusive.

5. The method of claim 1 wherein the transfer buffer comprises tris(hydroxymethyl)aminomethane (tris) in the range of 250 mM to 350 mM inclusive, glycine in the range of 250 mM to 350 mM inclusive, and tricine in the range of 100 mM to 200 mM inclusive.

6. The method of claim 1 wherein the method transfers the at least one of separated proteins, polypeptides, or nucleic acids from the gel onto a polyvinylidene difluoride (PVDF) or nitrocellulose membrane.

7. The method of claim 1 wherein the gel is a polyacrylamide gel.

8. The method of claim 1 wherein the electroblotting of proteins and/or nucleic acids occurs in less than about 15 minutes.

9. The method of claim 1 wherein the electroblot transfer occurs using a current greater than 20 mA/cm$^2$.

10. The method of claim 1 wherein the transfer buffer further comprises tris(hydroxymethyl)aminomethane (tris).

11. The method of claim 1 wherein the transfer buffer further comprises ethylenediaminetetraacetic acid (EDTA).

12. The method of claim 1 wherein the transfer buffer comprises ethylenediaminetetraacetic acid (EDTA) in the range of 1 mM to 100 mM inclusive.

13. The method of claim 1 wherein the absorbent material saturated with the transfer buffer provides a source of ions, and wherein said ions of said saturated absorbent material drive said transfer.

14. An electroblotting method comprising:
    saturating absorbent material with a transfer buffer comprising N-(2-hydroxy-1,1-bis(hydroxymethyl)ethyl)glycine (tricine) and glycine;
    sandwiching a membrane and a gel, the gel containing at least one of separated proteins, peptides, or nucleic acids, between at least two layers of the absorbent material saturated with the transfer buffer, to form a semi-dry stack; and
    applying a current greater than or equal to 20 mA/cm$^2$ in a semi-dry blotting procedure to transfer the separated proteins, peptides, and/or nucleic acids from the gel to the membrane.

15. The method of claim 14 wherein the transfer buffer further comprises tris(hydroxymethyl)aminomethane (tris).

16. The method of claim 14 wherein the transfer buffer further comprises ethylenediaminetetraacetic acid (EDTA).

17. The method of claim 14 wherein the absorbent material saturated with the transfer buffer provides a source of ions, and wherein said ions of said saturated absorbent material drive said transfer.

18. The method of claim 14 wherein the absorbent material is a cotton cellulose paper.

19. The method of claim 14 wherein the absorbent material is polyester cellulose.

20. The method of claim 14 wherein the transfer buffer comprises tris in the range of 250 mM to 1,000 mM inclusive, glycine in the range of 250 mM to 1,000 mM inclusive, and N-(2-hydroxy-1,1-bis(hydroxymethyl)ethyl)glycine (tricine) in the range of 100 mM to 1,000 mM inclusive.

21. The method of claim 14 wherein the transfer buffer comprises tris(hydroxymethyl)aminomethane (tris) in the range of 250 mM to 350 mM inclusive, glycine in the range of 250 mM to 350 mM inclusive, and tricine in the range of 100 mM to 200 mM inclusive.

* * * * *